United States Patent [19]

Uchida

[11] Patent Number: 5,214,031

[45] Date of Patent: May 25, 1993

[54] GROWTH-INHIBITORY FACTOR OBTAINED FROM HUMAN BRAIN

[76] Inventor: Yoko Uchida, 27-14, Kumano-machi, Itabashi-ku, Tokyo, Japan

[21] Appl. No.: 696,051

[22] Filed: May 6, 1991

[30] Foreign Application Priority Data

May 9, 1990 [JP] Japan ............................ 2-119620
Dec. 13, 1990 [JP] Japan ............................ 2-410164
Dec. 13, 1990 [JP] Japan ............................ 2-410165

[51] Int. Cl.⁵ .................. A61K 97/02; C07K 7/00
[52] U.S. Cl. ............................ 514/12; 514/2; 514/21; 530/324; 530/399; 530/326; 930/120; 930/DIG. 820
[58] Field of Search ............... 514/2, 12, 21; 530/324, 530/399, 326; 930/120, DIG. 820

[56] References Cited

PUBLICATIONS

Uchida et al., *Neuron*, 7, 337-347, Aug. 1991.
Uchida et al., *Chem. Absts.*, 115 (23):253245w, 1991.

*Primary Examiner*—F. T. Moezie
*Attorney, Agent, or Firm*—Bierman and Muserlian

[57] ABSTRACT

Disclosed are a growth-inhibitory factor which is a pure protein extracted from human brain and having inhibitory action against neurotrophic activity and a cDNA coding for a protein existing in human brain and the lysate from *E. coli* transfected with the cDNA having growth-inhibitory action, and also a method of inducing growth-inhibiting activity for treatment of Alzheimer disease by using the protein.

4 Claims, 7 Drawing Sheets

Chromatogram on DEAE – sephacel column

C18 reverse phase HPLC chromatogram

UV absorption spectrum 1 2 3 4
28S- 
18S-

GROWTH-INHIBITORY FACTOR OBTAINED FROM HUMAN BRAIN

BACKGROUND OF THE INVENTION

This invention relates to a novel and useful pure protein which is extracted from the human brain and has growth inhibitory action, to a method of prophylaxis and therapy of Artzheimer disease using the protein, and to a novel and useful gene (whole length cDNA) coding for the above protein.

Amidst the society where many people are growing older, senile dementia is attracting attention, and many efforts have been done for prophylaxis and therapy thereof. Particularly, the senile dementia called Alzheimer disease occurs in the early old stage (ages of 50 to 60), and investigation of its cause and establishment of the therapeutical method thereof have been hastened.

According to the knowledges obtained to date, Alzheimer disease is an neurodegenerative disease having such pathological characteristics as senile plaques, neurofibrillary tangles, etc. and a clinical characteristic of progressive dementia, and it may be considered that acceleration of metabolism and abnormal regeneration of neurons participate in that disease.

However, in the prior art, no effective prophylaxis method or therapeutical method of Alzheimer disease has been found and its established has been desired.

SUMMARY OF THE INVENTION

An object of the present invention is to provide a novel protein having a growth-inhibitory action effective for therapy of Alzheimer disease.

Another object of the present invention is to provide a method of inducing growth-inhibitory activity in humans by using the novel protein.

Further object of the present invention is to provide a gene (whole length cDNA) coding for the novel protein, which is useful for detection and preparation of the protein and also useful for diagnosis of Alzheimer disease.

One of the present inventors in the process of study about the components in the brains of Alzheimer disease patients has found a novel protein which exists in the brains of normal persons but will no longer exist in the brains of Alzheimer disease patients and has growth-inhibitory action, and successfully isolated the pure protein.

More specifically, the protein can be purified and collected from the extract from the human brain tissue as such or after concentration, according to combination of ultrafiltration, ion exchange chromatography, gel filtration, high performance liquid chromatography, specifically according to, for example, the method shown below in Examples.

DESCRIPTION OF THE PREFERRED EMBODIMENTS

Figure 1:
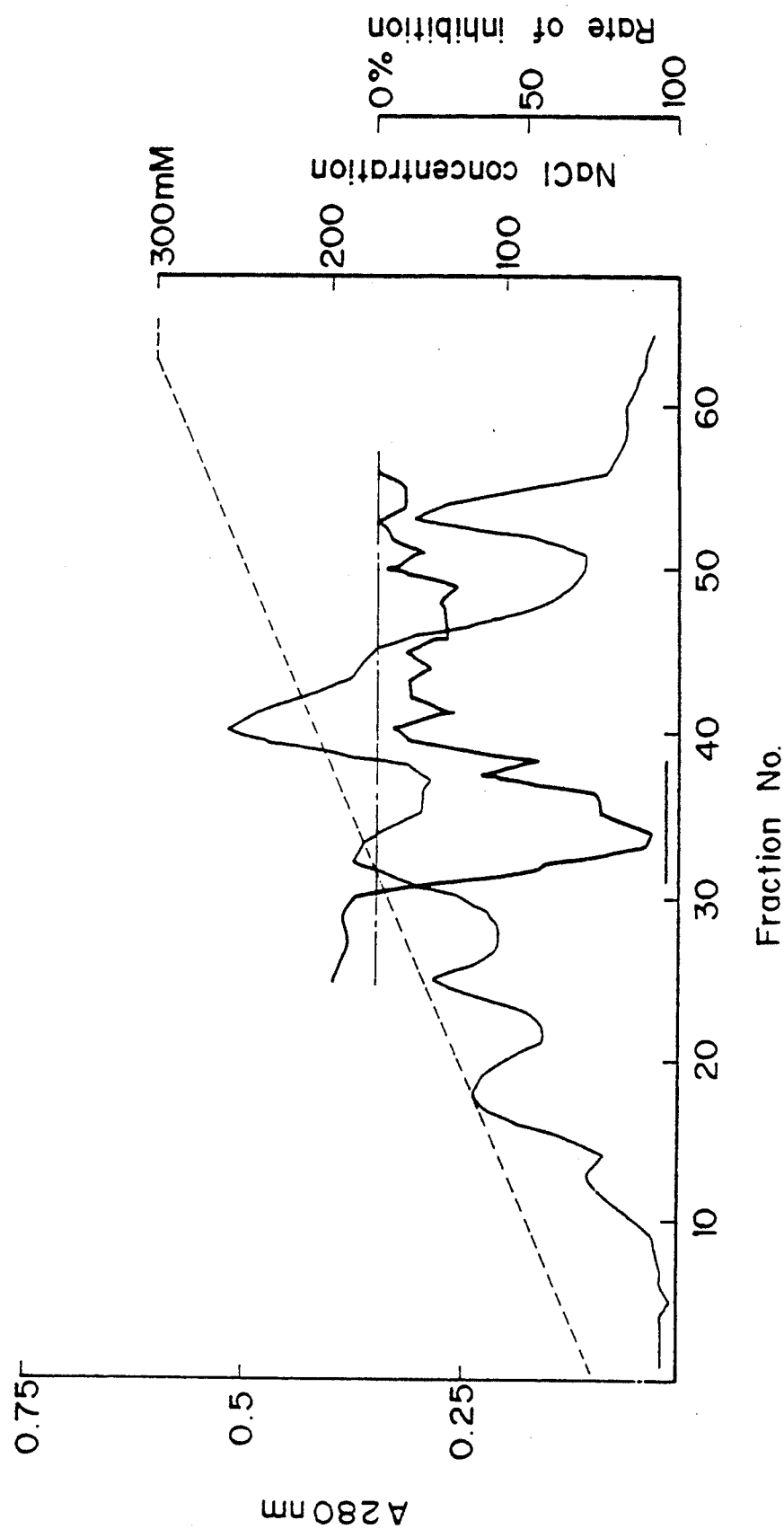
FIG. 1 shows a chromatogram on a DEAE Sephacel column of a fraction having a molecular weight of 10 kilodaltons or more obtained by homogenizing normal human cerebral cortex followed by ultrafiltration.

The novel protein of the present invention thus obtained has the following characteristics.

Molecular weight: about 5,000 (according to the SDS-polyacrylamide gel electrophoretic method)
Property: white amorphous powder
Stable pH range 3.0–7.7
Thermal stability: growth-inhibitory action maintained even when incubated at 37° C. for 20 hours or heated at 100° C. for 5 minutes.

The physiological activity of the novel protein of the present invention, namely the growth-inhibitory action was measured according to the method shown below in the test example.

Further, the whole amino acid sequence of the novel protein was determined according to the method shown below in Examples. As the result, the present substance was found to have the whole amino acid sequence shown below.

(SEQ ID NO.: 1)

```
 1                 5                10
Met Asp Pro Glu Thr Cys Pro Cys Pro Ser
11                15               20
Gly Gly Ser Cys Thr Cys Ala Asp Ser Cys
21                25               30
Lys Cys Glu Gly Cys Lys Cys Thr Ser Cys
31                35               40
Lys Lys Ser Cys Cys Ser Cys Cys Pro Ala
41                45               50
Glu Cys Glu Lys Cys Ala Lys Asp Cys Val
51                55               60
Cys Lys Gly Gly Glu Ala Ala Glu Ala Glu
61                65       68
Ala Glu Lys Cys Ser Cys Cys Gln,
```

As shown by the test example shown below, he novel protein exhibits growth-inhibitory action and it can be understood to be a substance for use in diagnosis, prophylaxis or therapy of Alzheimer disease. In order to induce growth-inhibitory activity in humans for the prophylaxis or therapy of Alzheimer disease, the novel protein according to the present invention may be introduced into humans.

For example, a growth-inhibiting effective amount of the protein may be administered ventricularly.

The effective amount of the protein depends on the age, body weight, syndrome, etc. of a person to be treated.

However, for treatment of a person having a body weight of 50 kg, the protein according to the present invention may usually be administered ventricularly by supplying, continuously for two weeks, a solution or dispersion thereof in a concentration of 25 mg/ml at a flow rate of 1 μl (microliter) per hour by using a minipump.

Since the protein is a substance existing in minute amount in human brain, the present inventors have thought of finding out a gene controlling production of the novel protein, producing the novel protein in a large amount according to genetic engineering and carrying out diagnosis, prophylaxis and therapy of Alzheimer disease by use thereof, studied intensively, and consequently found the gene (whole length cDNA) coding for the protein and successfully determined its nucleic acid sequence.

Separation of the gene in the present invention and determination of its nucleic acid sequence can be performed according to the methods specifically shown below in Examples.

The nucleic acid sequence of the cDNA coding for the growth-inhibitory factor in human brain thus determined was as follows.

```
ATG GAC CCT GAG ACC TGC CCC TGC CCT TCT GGT GGC TCC TGC ACC TGC  48    (SEQ ID NO.: 2)
GCG GAC TCC TGC AAG TGC GAG GGA TGC AAA TGC ACC TCC TGC AAG AAG  96
AGC TGC TGC TCC TGC TGC CCT GCG GAG TGT GAG AAG TGT GCC AAG GAC 144
TGT GTG TGC AAA GGC GGA GAG GCA GCT GAG GCA GAA GCA GAG AAG TGC 192
AGC TGC TGC CAG                                                  204,
```

The novel protein as described above is serviceable for diagnosis, therapy of Alzheimer disease, and the cDNA coding for the protein is a gene useful for enabling bulk production of the protein according to genetic engineering. The gene is also useful for diagnosis of Alzheimer disease, and further expected to be useful for therapy of Alzheimer disease by introducing directly the gene.

The present invention is described in more detail by referring to Examples.

EXAMPLE 1

Separation and purification of the present substance 20 g of gray matter of normal human cerebral cortex was homogenized with 60 ml of water, and centrifuged at 20,000 g for one hour to obtain 55 ml of the centrifuged supernatant.

Figure 2:
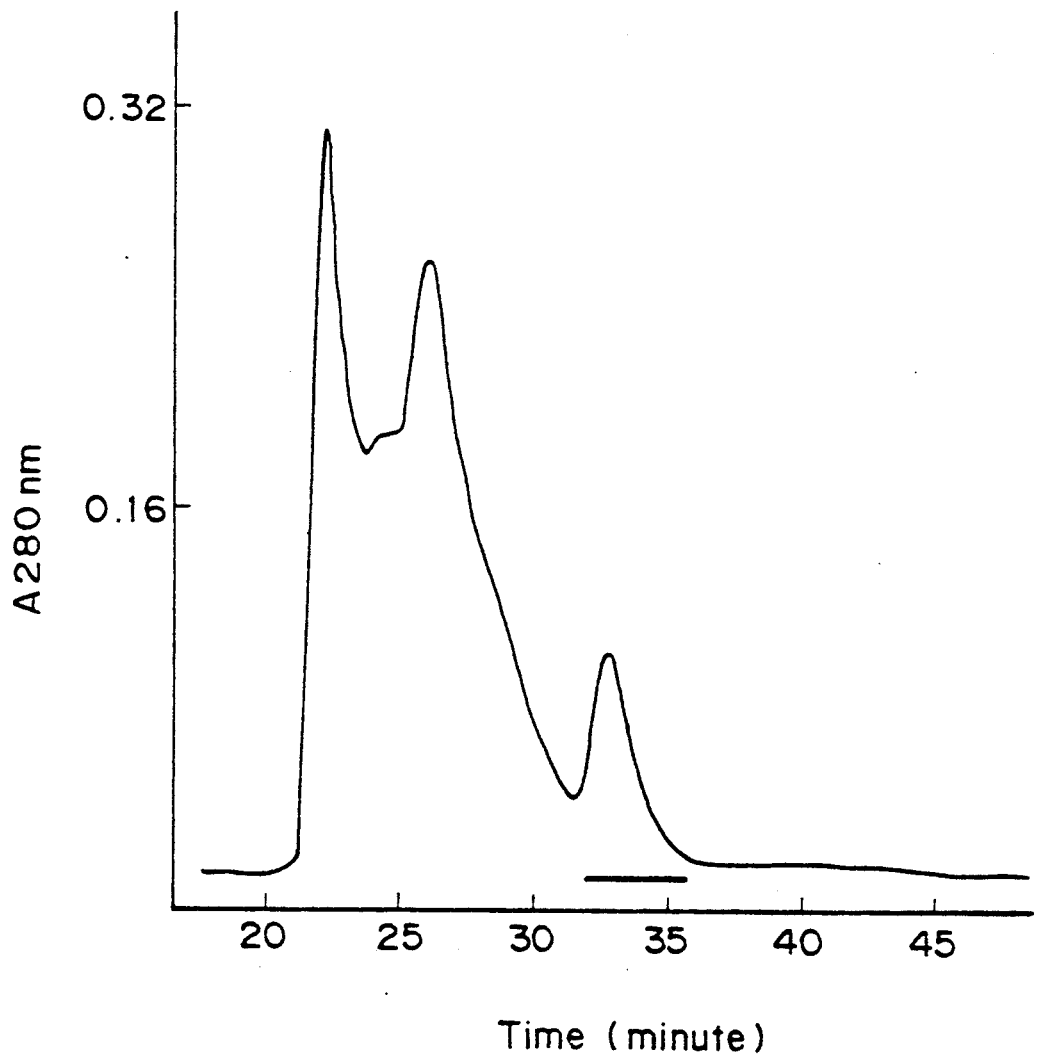
FIG. 2 shows a chromatogram of the DEAE-Sephacel fraction having inhibitory activity subjected to gel filtration.
Figure 3:
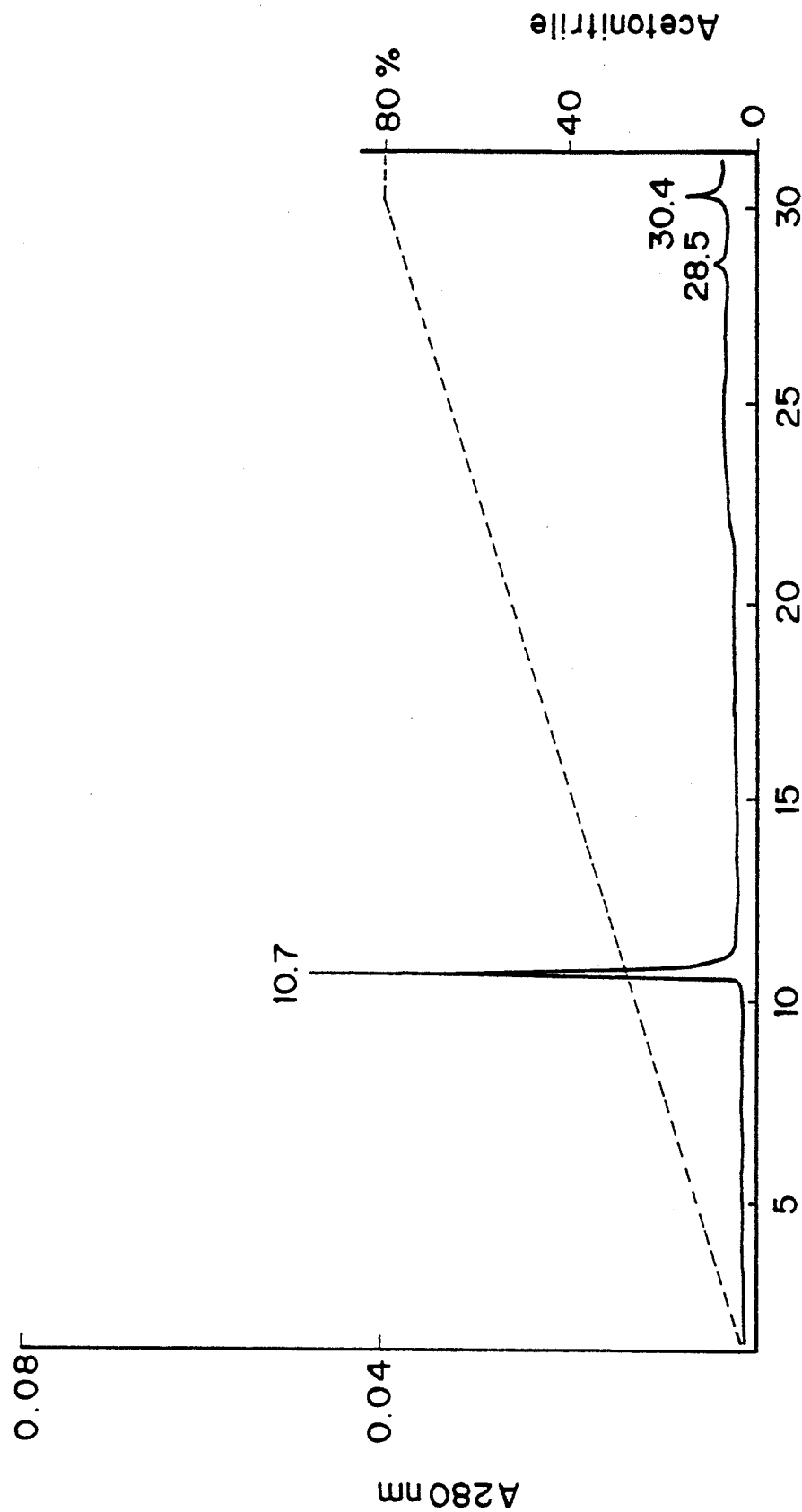
FIG. 3 shows a chromatogram of the gel filtration fractions having inhibitory activity applied to the C18 reverse phase HPLC.

The supernatant obtained (55 ml) was subjected to ultrafiltration by use of Amicon YM-10 film (trade name), a fraction having a molecular weight of 10 kilodaltons or more were applied onto a DEAE-Sephacel column (1.6 cmφ × 16 cm, Pharmacia), washed with 200 ml of a washing buffer (50 mM NaCl, 20 mM Tris-Cl (pH 7.6)), and then extracted with 320 ml of a 20 mM Tris-Cl (pH 7.6) with a linear concentration gradient of NaCl from 50 mM to 300 mM. The chromatogram according to the above-mentioned DEAE-Sephacel column is shown in FIG. 1. The fractions having the inhibitory activity from Fraction No. 31 to 38 were collected (40 ml), concentrated with Ficoll 400 after dialysis, then subjected to gel filtration with TSK G2000SW (Toso) (column size 7.5 mmφ × 6 cm), and the active fractions from Fraction No. 30 to 32 were collected (2.5 ml), followed by dialysis against 5 mM phosphate buffer (pH 7.4). The results of the gel filtration chromatography by use of the above-mentioned TSK G2000SW are shown in FIG. 2. After the liquid was concentrated to 550 μl, the concentrate was applied to a C18 reverse phase HPLC column (4.6 mmφ × 25 cm, Senshu Kagaku K. K., Japan). For elution, 5 mM ammonium formate solutions with a linear gradient of acetonitrile from 0% to 80% were employed. The results of the C18 reverse phase HPLC chromatography are shown in FIG. 3. As shown in FIG. 3, substantially only one sharp peak was obtained according to the C18 reverse phase HPLC chromatography, whereby it can be understood that the substance of the present invention was isolated.

EXAMPLE 2

Measurement of characteristics

Various characteristics as shown below were measured for the substance obtained in Example 1.

(1) UV absorption spectrum

Figure 4:
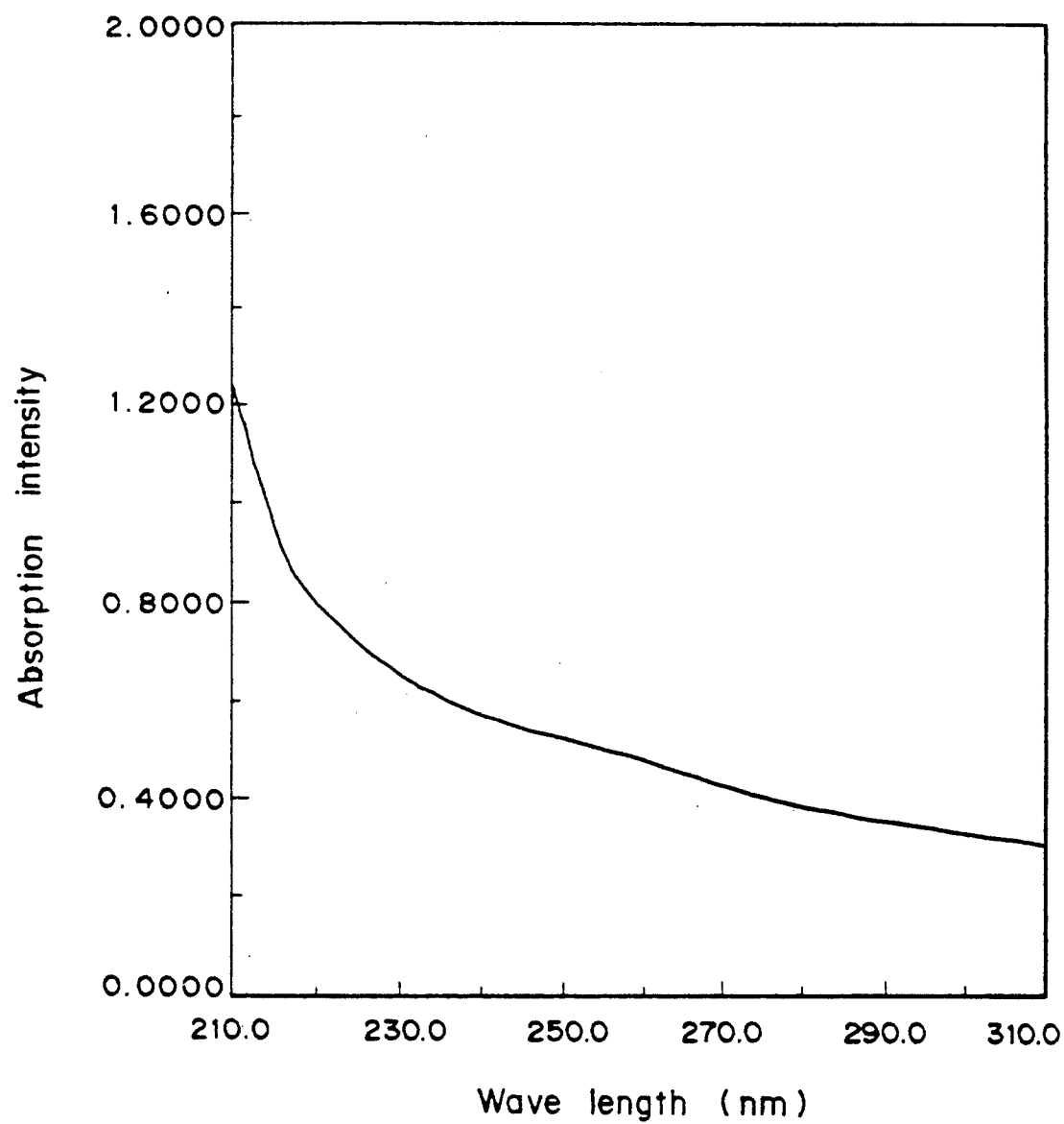
FIG. 4 shows a spectrum chart of the UV absorption spectrum of the substance (protein) of the present invention.

By use of a solution of 3 μg of the substance obtained in Example 1 in distilled water, the UV absorption spectrum was measured by a spectrophotomerter (DU65 Model, Beckman). The results are shown in FIG. 4.

(2) Stability

The substance obtained in Example 1 was prepared into an aqueous solution of 20 μg/ml, and trifluoroacetic acid was added to 10 μl of the solution to the final concentration of 0.1% (pH 3.0), heated to 37° C. for 20 hours and then lyophilized. The lyophilized product was dissolved in 10 μl of a phosphate buffer produced by Dulbecco (PBS (−)), and the inhibitory activity was assayed according to the method shown below in Example 3, but no reduction in inhibitory activity was recognized at all. Further, 100 μl of 2 μg/ml of the aqueous solution was taken, heated at 37° C. for 20 hours or at 100° C. for 5 minutes, and thereafter by use of 10 μl of the solution, stability test was conducted similarly as described above, whereby no reduction of inhibitory activity was recognized at all.

(3) Molecular weight

Figure 5:
FIG. 5 shows a SDS-PAGE electrophoresis pattern of the substance (protein) of the present invention.

An amount 5 μg of the substance obtained in Example 1 was dissolved in 10 μl of SDS-sample buffer, and by use of molecular weight markers (Chymotrypsinogen A (molecular weight 2,500), Chitochrome C (molecular weight 12,500), Aprotinin (molecular weight 6,500, Biorad), measurements were conducted with SDS-polyacrylamide gel electrophoresis with a concentration gradient from 7.5% to 20%, and consequently, it was identified to have a molecular weight of about 5,000 daltons. The results of the electrophoresis are shown in FIG. 5.

Test example Assay of neurotrophic activity inhibitory activity

Cells prepared from the cerebral cortex of newborn rats were seeded in number of 1.7 × 10⁴ on a microplate of 6 mm coated with gelatin-polyoruithine, and fed in a serum-free medium MEMN2 (Eagle's basal medium added with insulin, transferin, putrescine, progesteron, sodium selenite) containing 100 μl of the Alzheimer disease brain extract at the concentration of 125 μg/ml and 20 ng of the substance obtained in Example 1 in a 5% carbon dioxide gas cultivation tank at 37° C. for 5 days. After fixing with p-formaldehyde and 90% methanol/5% acetic acid solution, the MAP2 amount was quantitated by ELISA by using microtuble-attached protein 2 (MAP2) antibody (Amersham). On the other hand, the MAP2 amount of the culture with only addition of the Alzheimer disease brain extract was quantitated, and the inhibitory activity was represented by what % of the MAP2 amount was reduced.

Figure 6:
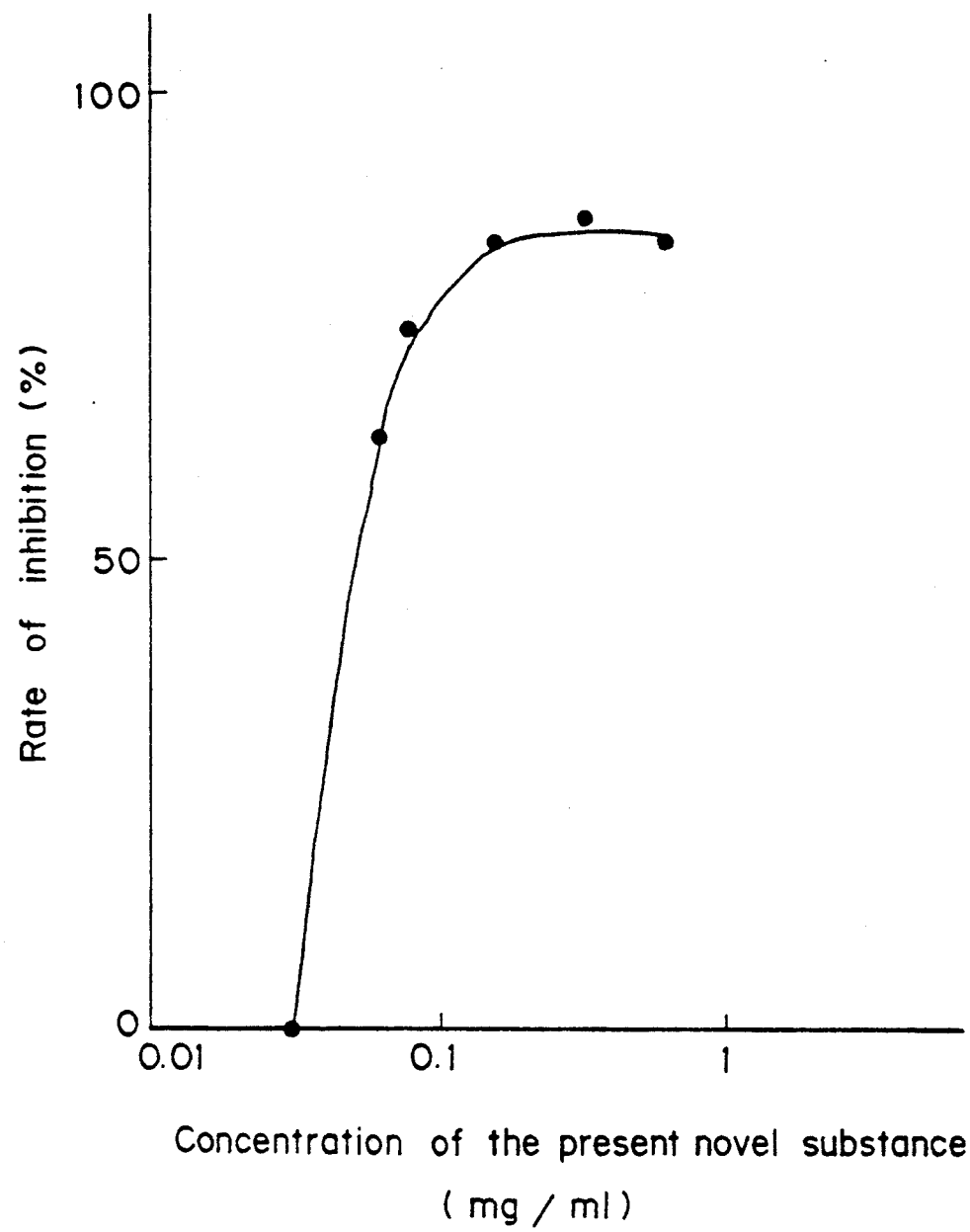
FIG. 6 shows dose-response curves for growth-inhibitory activity at each step of purifications for the substance of the present invention.
Figure 7:
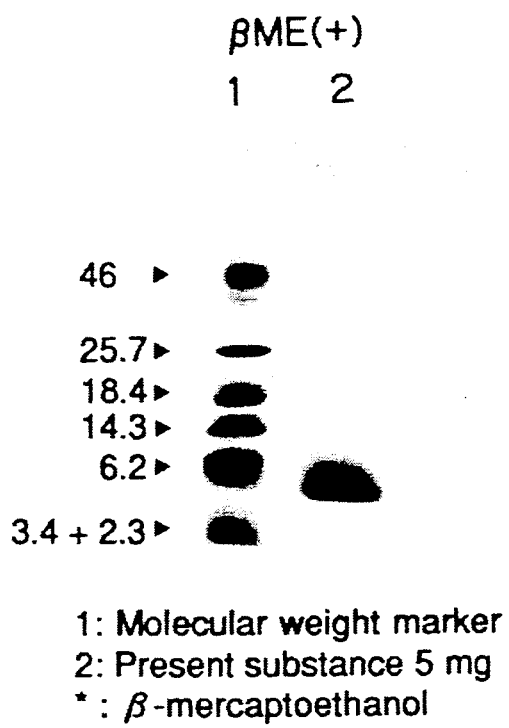
FIG. 7 shows results of the Northern analysis with the use of cDNA for the human growth-inhibitory factor (inhibitory factor for neuronal survival and neurite formation) as a probe. It is a chromatogram showing that the amount of the messenger RNA for the growth-inhibitory factor is reduced in Alzheimer disease.

By use of the method as described above, the relationship between the amount of the present substance and the growth-inhibition was measured. The results are shown in FIG. 6. As shown in FIG. 6, the inhibitory activity became equilibrated at the concentration of 0.2 μg/ml of the present substance, and its inhibitory activity was about 90%.

EXAMPLE 3

Analysis of amino acid sequence

An amount 200 μg of the substance obtained in Example 1 was pyridylethylated in a conventional manner. The present substance pyridylethylated (50 μg) was subjected to cyanogen bromide cleavage in a conventional manner. The present substance pyridylethylated was dissolved in 100 μl of a 0.1M Tris-Cl (pH 8.0) solution, 0.5 g of TPCK-trypsin (Sigma) or endoproteinase Asp-N (Behlinger) or S. aureus V8 protease (Sigma) was added, followed by incubation at 37° C. for 5 hours. The peptide fragments obtained by the four kinds of methods as described above were each subjected to separation according to the C18 reverse phase HPLC (0–80% acetonitrile/0.1% trifluoroacetic acid solution), and analyzed by using a protein sequencer (Model 477A, Applied Biosystems), and the retention time of the peak obtained and that of the standard substance were compared to determined the whole amino acid sequence of the present substance. As the result, the present substance was found to have the following whole amino acid sequence.

(SEQ ID NO.: 1)

```
 1               5              10
Met Asp Pro Glu Thr Cys Pro Cys Pro Ser
11              15              20
Gly Gly Ser Cys Thr Cys Ala Asp Ser Cys
21              25              30
Lys Cys Glu Gly Cys Lys Cys Thr Ser Cys
31              35              40
Lys Lys Ser Cys Cys Ser Cys Cys Pro Ala
41              45              50
Glu Cys Glu Lys Cys Ala Lys Asp Cys Val
51              55              60
Cys Lys Gly Gly Glu Ala Ala Glu Ala Glu
61              65              68
Ala Glu Lys Cys Ser Cys Cys Gln,
```

EXAMPLE 4

Separation of the present gene

On the basis of the amino acid sequence of the growth-inhibitory factor extracted from human brain, two oligonucleotides 5'ATGGATCC-CGAGACCTGCCC, (SEQ ID NO.:3) 5'CTGGCAG-CAGCTGCACTTCTC (SEQ ID NO.: 4) were synthesized, and with the use of these as the primer, cDNA was formed with a reverse transcriptase with the messenger RNA prepared from human brain as the template, and then the polymerase chain reaction was carried out. The reaction product was subcloned into the plasmid vector pUC19, the base sequence thereof was determined, and this was identified to be coincident with the amino acid sequence of the growth-inhibitory factor.

By use of the cDNA library prepared corresponding to the messenger RNA of normal human brain, 1×10⁶ clones were grown on a plate, transferred onto a nitrocellulose film, the above-mentioned subcloned nucleic acid sequence was labelled with $^{32}P$ to prepare a probe, which was subjected to hybrid formation onto the above-mentioned nitrocellulsoe film in a hybridization solution containing 50% formamide, 5XSSC (0.15M NaCl, 0.15M sodium citrate, pH 7.0) at 42° C. for 18 hours. Then, the filter was washed, and finally 0.1×SSC (0.15M NaCl, 15 mM sodium citrate, pH 7.0) autoradiography was performed at 55° C., and 24 cDNA's specific for the above-mentioned probe were isolated. The base sequence of the cDNA was determined, and as the result the existence of the nucleic acid sequence coding for the 68 amino acids was found.

EXAMPLE 5

The respective messenger RNA's were extracted, and each two micrograms thereof was subjected to electrophoresis in a modified Agarose gel, then transferred onto a nitrocellulose film, subjected to hybrid formation in the same hybridization solution as mentioned above with the above-mentioned cDNA as the probe at 42° C. for 18 hours. Then, the filter was washed with a filter, and finally with 0.1×SSC, 0.1% SDS at 65° C., followed by autoradiography. As the result, in Alzheimer disease, normal brain, a messenger RNA with a size of about 500 bp was recognized, and the amount of the messenger RNA was found to be reduced in Alzheimer disease.

---

What is claimed is:

1. A pure protein having a growth-inhibitory activity extracted from the human brain having a molecular weight of about 5000 (according to the SDS-polyacrylamide gel electrophoretic method) in the form of a white powder stable at a pH of 3.0 to 7.7 and thermally stable after incubation at 37° C. for 20 hours and after heating at 100° C. for 5 minutes.

2. The protein of claim 1 having a partial amino acid sequence of Asp Cys Val Cys Lys Gly Gly Glu Ala Ala Glu Ala Glu Ala Glu Lys Cys Ser Cys Cys Gln, (SEQ ID NO.:5).

3. The protein of claim 1 having the whole amino acid sequence of (SEQ ID NO.: 1)

```
 1                  5                 10
Met Asp Pro Glu Thr Cys Pro Cys Pro Ser
11                 15                 20
Gly Gly Ser Cys Thr Cys Ala Asp Ser Cys
21                 25                 30
Lys Cys Glu Gly Cys Lys Cys Thr Ser Cys
31                 35                 40
Lys Lys Ser Cys Cys Ser Cys Cys Pro Ala
41                 45                 50
Glu Cys Glu Lys Cys Ala Lys Asp Cys Val
51                 55                 60
Cys Lys Gly Gly Glu Ala Ala Glu Ala Glu
61                 65        68
Ala Glu Lys Cys Ser Cys Cys Gln,.
```

4. A method of inducing growth-inhibiting activity in a human in need thereof comprising administering to said human being a neurotrophically inhibiting effective amount of the protein of claim 1.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 68 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:

(A) ORGANISM: Homo sapiens
(F) TISSUE TYPE: Cerebral cortex (ix) FEATURE:
(A) NAME/KEY: Peptide
(B) LOCATION: 1..68
(D) OTHER INFORMATION: /note="Growth inhibitory activity on brain cells"

(xi) SEQUENCE DESCRIPTION: SEQ ID NO:1:

| Met | Asp | Pro | Glu | Thr | Cys | Pro | Cys | Pro | Ser | Gly | Gly | Ser | Cys | Thr | Cys |
|---|---|---|---|---|---|---|---|---|---|---|---|---|---|---|---|
| 1 | | | | 5 | | | | | 10 | | | | | 15 | |
| Ala | Asp | Ser | Cys | Lys | Cys | Glu | Gly | Cys | Lys | Cys | Thr | Ser | Cys | Lys | Lys |
| | | | 20 | | | | | 25 | | | | | 30 | | |
| Ser | Cys | Cys | Ser | Cys | Cys | Pro | Ala | Glu | Cys | Glu | Lys | Cys | Ala | Lys | Asp |
| | | 35 | | | | | 40 | | | | | 45 | | | |
| Cys | Val | Cys | Lys | Gly | Gly | Glu | Ala | Ala | Glu | Ala | Glu | Ala | Glu | Lys | Cys |
| | 50 | | | | | 55 | | | | | 60 | | | | |
| Ser | Cys | Cys | Gln |
| 65 | | | |

(2) INFORMATION FOR SEQ ID NO:2:

(i) SEQUENCE CHARACTERISTICS:
(A) LENGTH: 204 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Homo sapiens
(F) TISSUE TYPE: Cerebral cortex (ix) FEATURE:
(A) NAME/KEY: matpeptide
(B) LOCATION: 1..204
(C) IDENTIFICATION METHOD: experimental
(D) OTHER INFORMATION: /function="Inhibits growth of brain cells"
/ product="GROWTH INHIBITORY FACTOR"
/ evidence=EXPERIMENTAL (xi) SEQUENCE DESCRIPTION: SEQ ID NO:2:

```
ATGGACCCTG AGACCTGCCC CTGCCCTTCT GGTGGCTCCT GCACCTGCGC GGACTCCTGC    60
AAGTGCGAGG GATGCAAATG CACCTCCTGC AAGAAGAGCT GCTGCTCCTG CTGCCCTGCG   120
GAGTGTGAGA AGTGTGCCAA GGACTGTGTG TGCAAAGGCG GAGAGGCAGC TGAGGCAGAA   180
GCAGAGAAGT GCAGCTGCTG CCAG                                         204
```

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Homo sapiens
(F) TISSUE TYPE: Cerebral cortex (ix) FEATURE:
    (A) NAME/KEY: primerbind
    (B) LOCATION: 1..20
    (D) OTHER INFORMATION: /standardname="Oligonucleotide
        primer to make cDNA from genomic mRNA"

(xi) SEQUENCE DESCRIPTION: SEQ ID NO:3:

ATGGATCCCG AGACCTGCCC                                                    20

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (F) TISSUE TYPE: Cerebral cortex (ix) FEATURE:
        (A) NAME/KEY: primerbind
        (B) LOCATION: 1..21
        (D) OTHER INFORMATION: /standardname="Oligonucleotide
            primer to make cDNA from genomic mRNA"

(xi) SEQUENCE DESCRIPTION: SEQ ID NO:4:

CTGGCAGCAG CTGCACTTCT C                                                  21

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:
        (A) ORGANISM: Homo sapiens
        (F) TISSUE TYPE: Cerebral cortex (ix) FEATURE:
        (A) NAME/KEY: Peptide
        (B) LOCATION: 1..21
        (D) OTHER INFORMATION: /note="Partial amino acid sequence
            of the growth inhibitory factor"

(xi) SEQUENCE DESCRIPTION: SEQ ID NO:5:

Asp Cys Val Cys Lys Gly Gly Glu Ala Ala Glu Ala Glu Ala Glu Lys
1               5                   10                  15

Cys Ser Cys Cys Gln
                20